(12) United States Patent
Erikstrup

(10) Patent No.: US 10,390,921 B2
(45) Date of Patent: Aug. 27, 2019

(54) URINE FLOW CONTROL SYSTEM AND A MAGNETIC ACTUATOR DEVICE

(71) Applicant: MAGCATH APS, Copenhagen K (DK)

(72) Inventor: Niels Erikstrup, Zug (CH)

(73) Assignee: MAGCATH APS, Copenhagen K (DK)

( * ) Notice: Subject to any disclaimer, the term of this patent is extended or adjusted under 35 U.S.C. 154(b) by 179 days.

(21) Appl. No.: 15/311,408

(22) PCT Filed: May 27, 2015

(86) PCT No.: PCT/DK2015/050133
§ 371 (c)(1),
(2) Date: Nov. 15, 2016

(87) PCT Pub. No.: WO2015/180730
PCT Pub. Date: Dec. 3, 2015

(65) Prior Publication Data
US 2017/0105826 A1    Apr. 20, 2017

(30) Foreign Application Priority Data

May 28, 2014  (DK) .................................. 2014 70306
Aug. 22, 2014  (DK) .................................. 2014 70506

(51) Int. Cl.
*A61F 2/00*   (2006.01)
*A61M 25/00*  (2006.01)
*A61F 5/451*  (2006.01)

(52) U.S. Cl.
CPC ............ *A61F 2/0018* (2013.01); *A61F 5/451* (2013.01); *A61M 25/0075* (2013.01); *A61M 2025/0076* (2013.01); *A61M 2025/0078* (2013.01)

(58) Field of Classification Search
CPC ...... A61F 2/0018; A61F 5/451; A61F 2/0009; A61M 25/0075; A61M 2025/0078; A61M 2025/0076
See application file for complete search history.

(56) References Cited

U.S. PATENT DOCUMENTS 3,812,841 A    5/1974  Isaacson
5,030,199 A    7/1991  Barwick et al.
(Continued)

FOREIGN PATENT DOCUMENTS

EP           0700668         3/1996

OTHER PUBLICATIONS

International Search Report on corresponding PCT application (PCT/DK2015/050133) from International Searching Authority (EPO) dated Oct. 15, 2015.
(Continued)

*Primary Examiner* — Kaylee R Wilson
(74) *Attorney, Agent, or Firm* — Klein, O'Neill & Singh, LLP

(57) ABSTRACT

The invention relates to a urine flow control system (50) including a catheter device (10, 100) for insertion into a urethra, the catheter device (10, 100) having: a proximal end portion (14) and an opposite distal end portion (16, 102), a conduit (C) between said proximal end portion (14) and said distal end portion (16) having a urine inlet opening (2) at said proximal end portion (14) and a urine outlet opening (4, P) at said distal end portion (16, 102), and a magnetically actuatable valve located at said distal end portion (16, 102) for controlled discharge of urine from said catheter device (10, 100) through said outlet opening (4, P), and a magnetic actuator device with an actuator magnet (201), separate from said catheter device (10, 100), for operating said valve, characterized in said magnetic actuator device (200) com-
(Continued)

prising a housing (205) for receiving urine discharged from said catheter device (10, 100), said housing (205) having a first open end (202) configured for receiving said distal end portion (16, 102) with said magnetically actuatable valve and said outlet opening (4, P), and a second end, said housing (205) having at said first end (202) said actuator magnet (201).

11 Claims, 6 Drawing Sheets

(56) References Cited

U.S. PATENT DOCUMENTS

| | | | | |
|---|---|---|---|---|
| 5,257,636 | A | * 11/1993 | White | A61M 25/0127 |
| | | | | 128/200.26 |
| 5,352,182 | A | * 10/1994 | Kalb | A61B 5/14507 |
| | | | | 600/30 |
| 5,624,374 | A | 4/1997 | Von Iderstein | |
| 6,213,936 | B1 | * 4/2001 | Nishioka | A61F 2/0009 |
| | | | | 600/29 |
| 2001/0034470 | A1 | 10/2001 | Whalen et al. | |

OTHER PUBLICATIONS

Written Opinion on corresponding PCT application (PCT/DK2015/050133) from International Searching Authority (EPO) dated Oct. 15, 2015.

\* cited by examiner

URINE FLOW CONTROL SYSTEM AND A MAGNETIC ACTUATOR DEVICE

CROSS-REFERENCE TO RELATED APPLICATIONS

This application is the national phase entry, under 35 U.S.C. Section 371(c), of International Application No. PCT/DK2015/050133, filed May 27, 2015, claiming priority from Danish Application Nos. PA 2014 70306, filed May 28, 2014 and PA 2014 70506, filed Aug. 22, 2014. The disclosures of the International Application and the Danish Applications from which this application claims priority are incorporated herein by reference in their entireties.

FEDERALLY SPONSORED RESEARCH OR DEVELOPMENT

Not Applicable

BACKGROUND

The present invention relates to an improved urine flow control system of the type involving the use of a magnetic valve body and magnetic actuator device, and to a magnetic actuator device for use in said system.

Incontinence is the inability of any of the physical organs to restrain discharges of their contents; in the present context, incontinence is considered the involuntary discharge or evacuation of urine. This could e.g. be during movement, such as jumping, or when sneezing or laughing where persons suffering from incontinence experience problems.

Persons suffering from incontinence are often compelled to wear a pad for collecting urine being discharged from the urethra. In addition, persons suffering from incontinence may experience that the discharge of urine causes unwanted odours, which may cause the person to feel uncomfortable and embarrassed. Therefore, there is a need for a device hindering uncontrolled discharge of urine.

Some persons, on the other hand, have problems emptying their bladder. This may be due to low detrusor activity, which is associated to neurological or myogenic conditions. It may also be due to patient age factors, medication or bladder outlet obstruction. Such patients insert catheters when emptying the bladder. Either they catheterize themselves, have nurses perform the catheterization, or they carry a catheter permanently.

Such patients may be helped by wearing a urine flow control system with a valve catheter, as this can eliminate the need for catheterization every time the bladder needs emptying.

US patent application 2001/0034470 and U.S. Pat. No. 5,030,199 show examples of prior art urine flow control systems or incontinence device, both involving a conduit for urethral installment as well as a magnetic actuator device allowing a user to control urine discharge. A user may control discharge of urine by manually holding the actuator device in the form of an actuator magnet close to the distal end of the conduit outside the urethra. In the prior art the actuator magnet is also referred to as a "portable activating magnet" which is configured to be placed in a pocket, a pocket book, or which can be formed in a decorative shape to be worn on a necklace or bracelet for convenient access. It may even be formed for retention in a key chain or as part of a ring.

One aspect of general importance to a user of an incontinence device is that discharge of urine should be possible to carry out in a highly hygienic manner. The fact that the prior art actuator magnet is hand held involves the risk that the user will soil herself as the actuator magnet is held close to the valve body, and this may be seen as a problem with those prior art catheter devices that have a magnetically actuatable drainage control valve.

The present invention aims at solving this problem and, hence, to increase the user-convenience experienced with the particular type of urine flow control systems referred to above which for many reasons would be expected to be more popular than non-magnetic catheter devices, such as those having a urine discharge conduits with a valve that must be squeezed manually to open it.

Broadly, the aforementioned problems are solved with a system and a magnetic actuator device as claimed. Preferred embodiments are defined in the dependent claims.

BRIEF DESCRIPTION OF THE DRAWINGS

In the following an embodiment of the invention will be described in more detail with reference to the drawings, wherein:

FIG. 8b is a cross/sectional view showing the encircled area in FIG. 8a.

DETAILED DESCRIPTION

It is emphasized that the urine flow control system discussed in the following may equally be used by an incontinent as well as a person suffering from problems emptying their bladder. For convenience, however, the urine flow control system of the invention will in the following be described in the context of incontinence devices.

Figure 1:
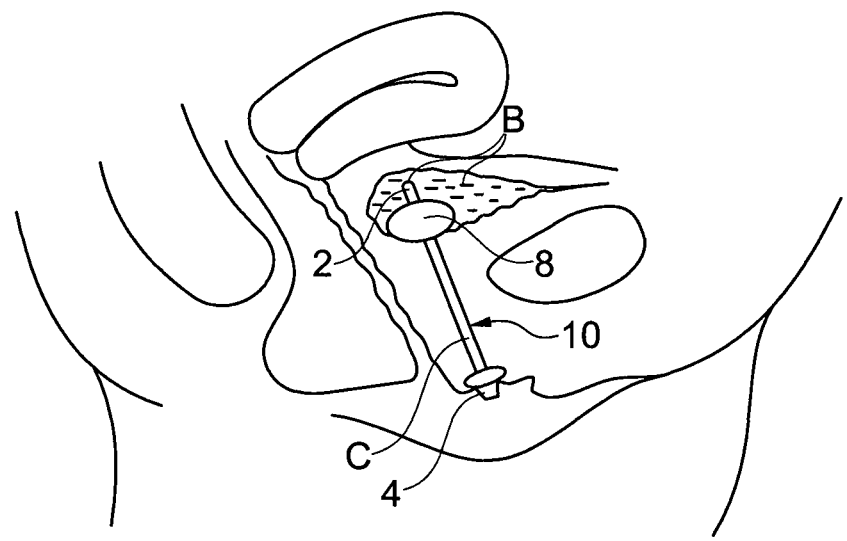
FIG. 1 is a simplified anatomical view showing the general location of an incontinence device in the urethra.

FIG. 1 shows an example of a prior art female incontinence control device in the form of a catheter device 10 with a urine discharge conduit C, the conduit C having an inlet opening 2 at the proximal end portion nearest bladder B of the catheter device 10 and an outlet opening 4 at the distal end portion thereof. To maintain the correct position of the catheter device 10 in the urethra use is made of a bladder engaging section 8 located at the proximal end portion of the catheter device 10. The bladder engaging section 8 may, as shown, be an inflatable balloon.

Figure 2:
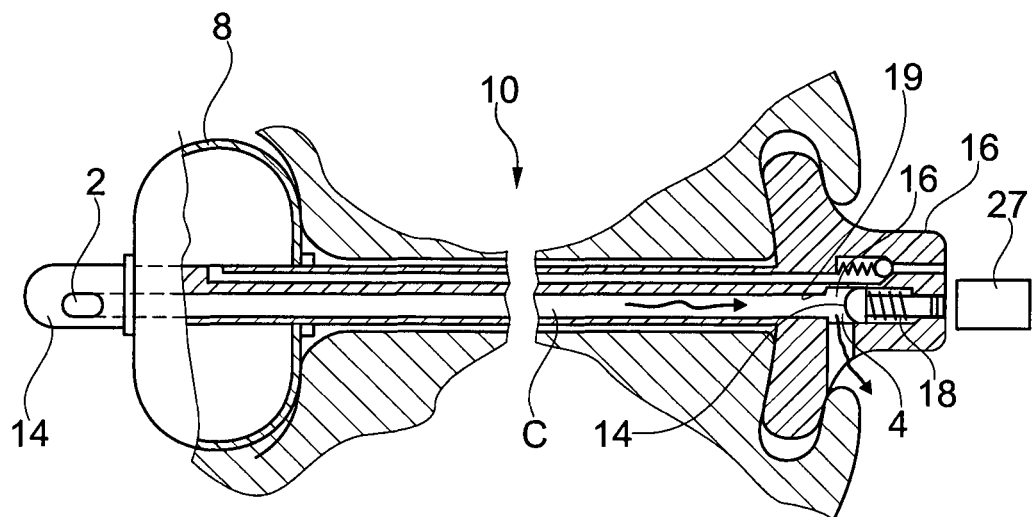
FIG. 2 is a sectional view showing a prior art incontinence device as shown in FIG. 1, located in the urethra.

The prior art catheter device 10 shown in FIG. 1 is illustrative of the general type of incontinence devices, or urine flow control devices, to which the present invention is related, namely where a magnetically actuatable drainage control valve is included to seal off the urine discharge conduit C, as discussed below. In this way, a user may control discharge of urine by manually holding an actuator close to the distal end of the conduit C outside the urethra. This operation is shown in FIG. 2 where the actuator in the form of an actuator magnet is referenced by numeral 27. The magnetically actuatable drainage control valve includes a valve body 14 of a magnetically attractive or magnetized material, arranged in a chamber 16; in FIG. 2 the valve body 14 is biased by a spring 18 towards a closed position (not shown) resting against a valve seat 19 and preventing outflow of urine through the sideways oriented outlet opening 4 at the distal end portion. It will be understood that the magnetic force by actuator magnet 27 is such that the valve body 14 is drawn against the spring 18 towards its open position away from the valve seat 19, allowing sideways outflow of urine through the outlet opening 4 located at the distal end portion. When the actuator magnet 27 is removed, the valve closes again.

In the prior art the actuator magnet 27 shown in FIG. 2 is also referred to as a "portable activating magnet" which can be placed in a pocket, a pocket book, or which can be formed in a decorative shape to be worn on a necklace or bracelet for convenient access. It may even be formed for retention in a key chain or as part of a ring.

One aspect of general importance to a user of an incontinence device is that discharge of urine should be possible to carry out in a highly hygienic manner. The fact that the prior art actuator magnet 27 is hand held involves the risk that the user will soil herself as the actuator magnet 27 is held close to the valve body 14, and this may be seen as a problem with those prior art catheter devices that have a magnetically actuatable drainage control valve.

The present invention aims at solving this problem and, hence, to increase the user-convenience experienced with the particular type of magnetic catheter devices referred to above which for many reasons would be expected to be more popular than non-magnetic catheter devices, such as those having a urine discharge conduits with a valve that must be squeezed manually to open it.

The invention will in the following be discussed in connection with a novel catheter device 100 subject of a parallel patent application by the present inventor and which is shown partially in FIG. 3; however, it is stressed that any type of incontinence catheter device having a magnetically actuatable drainage control valve, such as that shown in FIG. 2, may normally form part of the present novel incontinence flow control system and be used in connection with the novel magnetic actuator device discussed in the following.

Figure 3:
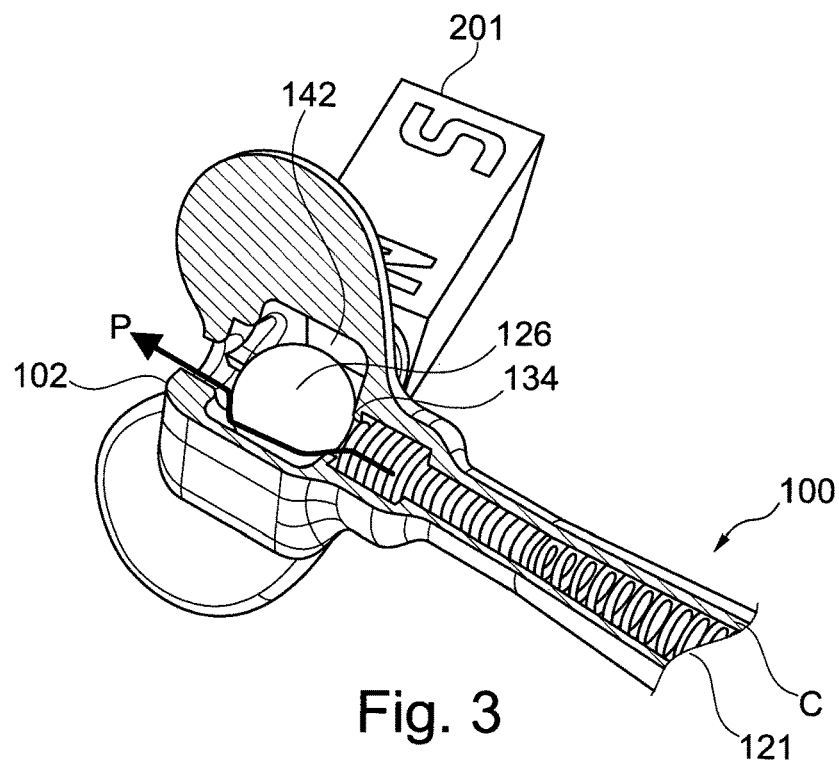
FIG. 3 shows a perspectival partial view of another incontinence device.

Shown in FIG. 3 is an incontinence device 100 having a urine discharge conduit C and a metal coil 121 which provides for stability of the device 100 and which also is magnetically attractive to attract a magnet acting as a valve body 126 towards a valve seat 134 near the end of the coil 121. The valve body 126 is mounted to be axially displaceable within a chamber 142 in the distal end portion 102 and defines, together with the valve seat 134 and metal coil 121, a magnetically actuatable valve. As an alternative, a spring located in the chamber 142 may be used to hold the valve body 126 against the valve seat 134.

In FIG. 3, for discharging urine a user has approached the valve body 126 with an actuator comprising an actuator magnet 201 held in her hand close to the distal end portion of the catheter device 100, which distal end portion 102 is located outside the urethra. The magnetic force from actuator magnet 201 is of such strength as to pull or displace the aforementioned magnet acting as valve body 126 away from the valve seat 134 to allow for an axial outflow of urine, as shown by the arrow P. By "axial outflow" is meant herein a flow of urine directed parallel with, substantially parallel with, the conduit C, in contrast to the "sideways outflow" discussed in relation to FIG. 2. As an alternative, the actuator may comprise a body of a magnetically attractive material, the overall object being to displace the magnet acting as valve body 126 by magnetic attraction. When the actuator is removed the valve recloses by the magnetic attraction driving the valve body 126 towards the valve seat 134.

Figure 4:
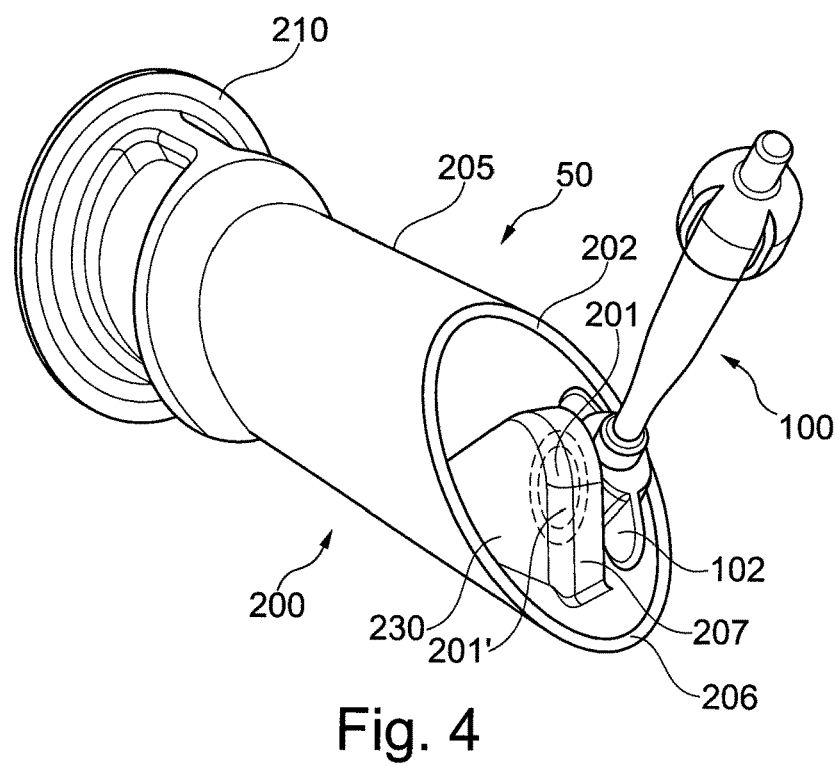
FIG. 4 shows the novel urine flow system according to the invention, including a magnetically activated catheter device and a magnetic actuator device.

FIG. 4 shows the catheter device 100 of FIG. 3 approximately in the position it would be in in the urethra, as shown in FIG. 1, and with its distal end portion 102 being received within the open end 202 of an embodiment of the novel magnetic actuator device 200 of the present invention, which comprises a tubular or essentially tubular housing 205 or funnel and a centrally located raised housing subportion 207 wherein an actuator as discussed above, be it a magnet 201 or a body 201' of a magnetically attractive material, is lodged.

FIG. 4 as such shows the novel urine flow system 50 according to the invention being the novel combination of a magnetically activated catheter device 100 with the novel magnetic actuator device 200. The raised subportion 207 defines a passage 230 on either side thereof, each passage 230 being delimited to the other side opposite the raised subportion 207 by a portion of the wall 206 of the housing 205.

Figure 5A:
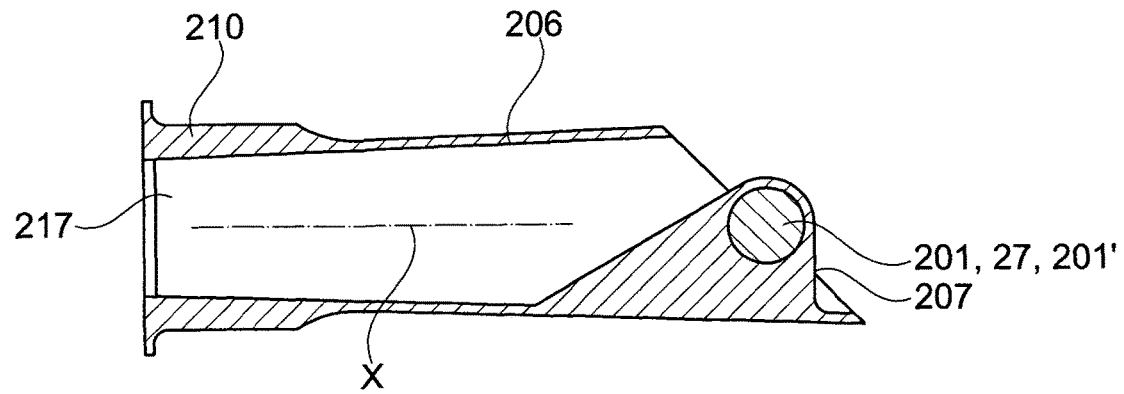
FIGS. 5a and 5b show, respectively, a sectional view of the magnetic actuator device and various types of actuator magnets for the magnetic actuator device.
Figure 5B:
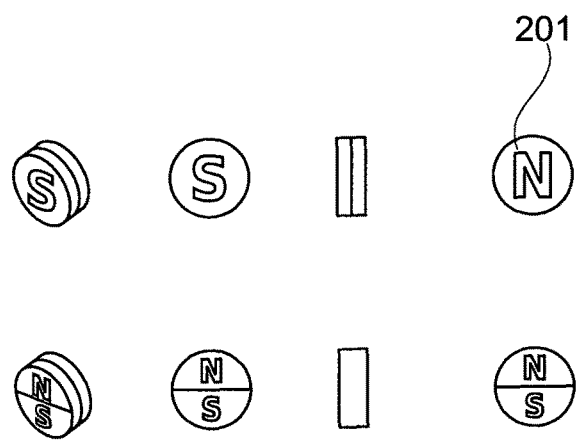

The housing 205 is preferably molded of a plastics material and is easy to rinse, and the actuator comprising a magnet 201 or a body 201' of a magnetically attractive material, may be embedded in the material forming the housing subportion 207 during the molding operation. Alternatively, the actuator comprising actuator magnet 201 or body 201 may be arranged, still centrally along the central axis X of the housing 205, with its surface directly exposed. FIG. 5a is a sectional view of the magnetic actuator device 200 and FIG. 5b shows various types of actuator magnets 201 for lodging in the housing subportion 207. In another embodiment the housing 205 is made of a biodegradable material and intended for single use.

Referring again to FIG. 4, when a female using the catheter device 100 wishes to discharge urine she will hold on to the outside gripping portion 210 of the magnetic actuator device 200 and move it towards the distal end portion 102 of the catheter device 100 which projects from the urethra. The magnetic actuator device 200 is configured to receive the distal end portion 102 of the catheter device 100 by simply moving it into the inside of the housing 205 through the open end 202, with or without contacting the housing wall 206 and without necessarily establishing any mechanical coupling between the catheter device 100 and the magnetic actuator device 200.

Common to the use of the present magnetic actuator device 200 with the general type catheter devices shown in FIGS. 2 and 3 is that as soon as the distal end portion with the urine outlet opening 4, P is received within the tubular housing 205 the catheter device valve opens as the valve body 14, 126, which is a magnet, is attracted by actuator magnet 201 or to body 201' of a magnetically attractive material, such that urine discharge into the interior of housing 205 through passage P, 4, respectively, is permitted. The skilled person will understand that the properties of the body 201' are selected such that there is a greater attractive force between the valve body 14, 126 and the body 201' than between the valve body 14, 126 and the valve seat 134, such that the valve body 14, 126 will seek towards the body 201' of the magnetically attractive material.

In this connection, it may sometimes be advantageous when the catheter device is of the type providing for an axial outflow, as in FIG. 3, but clearly the catheter device of FIG. 2 offering a sideways outflow may also be used as the housing wall 206 will prevent spillage of urine due to the location of the actuator 201, 201' centrally within the housing 205 in the embodiment of FIG. 4. As the skilled person will realize, in some combinations it may be desirable to position the actuator 201, 201' spaced a relatively large distance from the open end 202. This may be the case where there is a desire to insert the distal end portion 16, 102 deeper into the housing 205.

Figure 6A:
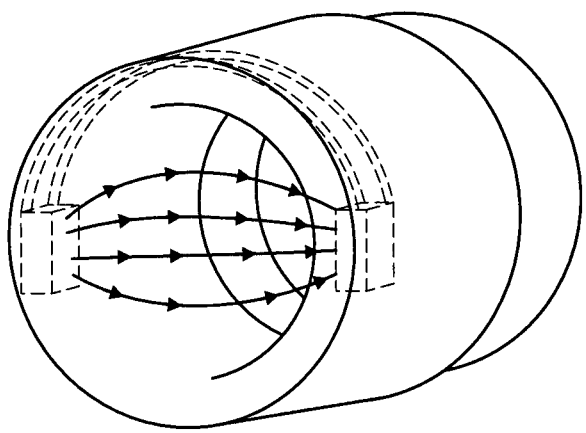
FIGS. 6a and 6b show perspective views of an embodiment incorporating a horseshoe magnet.
Figure 6B:
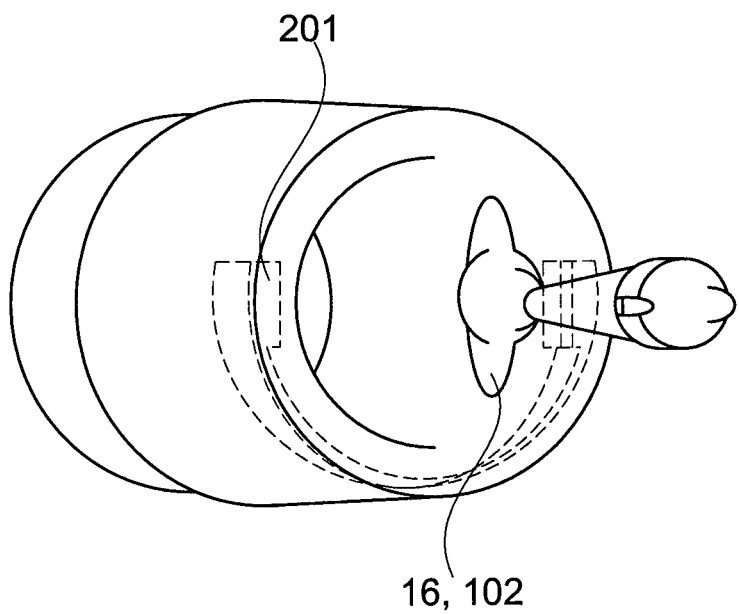

In some applications it may alternatively be preferred to embed or arrange the actuator, be it magnet 201 or body 201', in the peripheral wall 206 of the housing 205, with the actuator 201, 201' being shielded such that the magnetic field outside the housing 205 is of such low strength that the valve body 14, 126 will not be affected if the housing 205 is incorrectly held close to the catheter device 100 without the distal end portion thereof being received within the housing 205. FIGS. 6a and 6b show such an embodiment incorporating a horseshoe magnet embedded or otherwise arranged at the first open end 202; the magnetic field lines are such that the valve will more likely open for urine discharge when the distal end portion is received inside the housing 205 than outside.

Figure 7A:
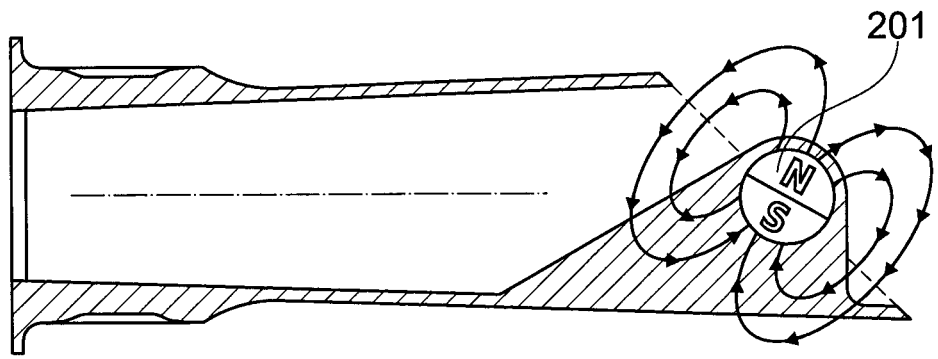
FIGS. 7a and 7b show field lines when using magnets of the two types shown in FIG. 5b.
Figure 7B:
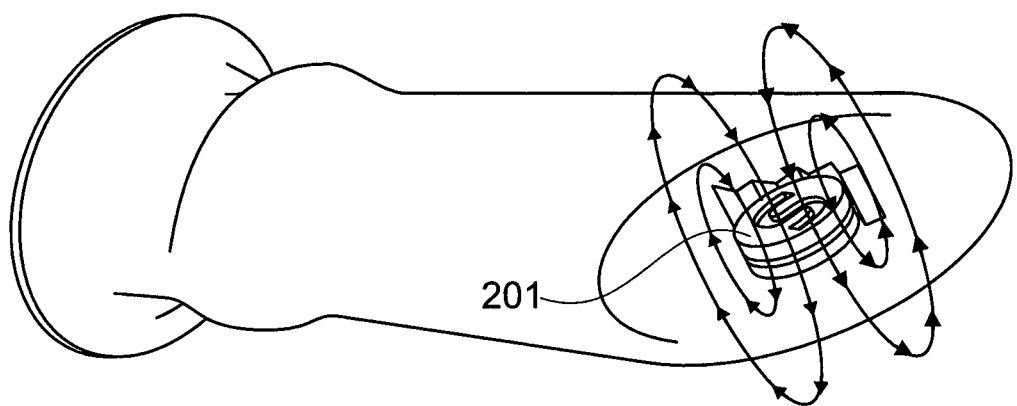

Preferably, the magnetic field lines and strength of the actuator magnet 201 are/is selected such that the valve will only open when the distal end portion of the catheter device, which projects from the urethra, is substantially or fully received in the housing 205 such that there is a high certainty that urine will be discharged into the elongated magnetic actuator housing 205 and flow along the length thereof. This means that the magnetically activatable drainage control valve will preferably not open if the magnetic actuator device 100 is merely brought close to the catheter device; only when the distal end portion of the catheter device is located within the housing 205 of the magnetic actuator device 200 will the valve open. FIGS. 7a and 7b show field lines when using magnets 201 of the two types shown in FIG. 5b. The embodiment of FIG. 7b may in some cases be preferred since the distal end portion 102 of the catheter device 10 will be drawn towards the projecting or raised subportion 207, leading to a higher degree of guidance of the housing 205 relative to the distal end portion 102, as the magnetic actuator device 200 is moved towards the catheter device 10, i.e. towards the distal end portion 102 thereof.

It is possible to form the housing 205 with a closed end opposite the open end 202, so that urine may be collected in a chamber in the housing 205, or alternatively to form the housing 205 with an aperture 217 opposite the open end 202 to allow urine to be immediately discharged into a toilet.

Preferably, the elongated housing 205 has a length in the order of 5 cm-15 cm and a width or diameter in the order of 0.4 cm-3 cm. A shorter housing 205 may also find use, such as where the user prefers to attach a flexible collection bag to the end of the housing 205 at aperture 217; such a bag may be of the type having a narrow opening that may be pulled over the housing wall 206 and attached thereto, such as by a rubber band or similar.

Figure 8A:
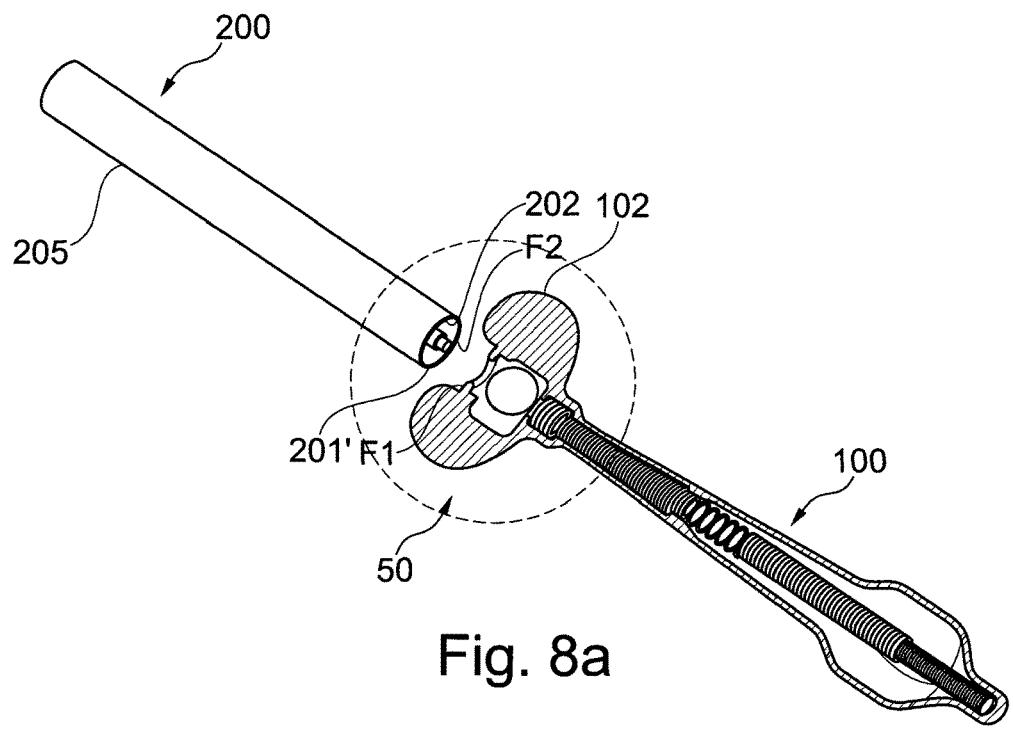
FIG. 8a is a perspective cross-sectional view showing a further embodiment of the present urine flow control system.
Figure 8B:
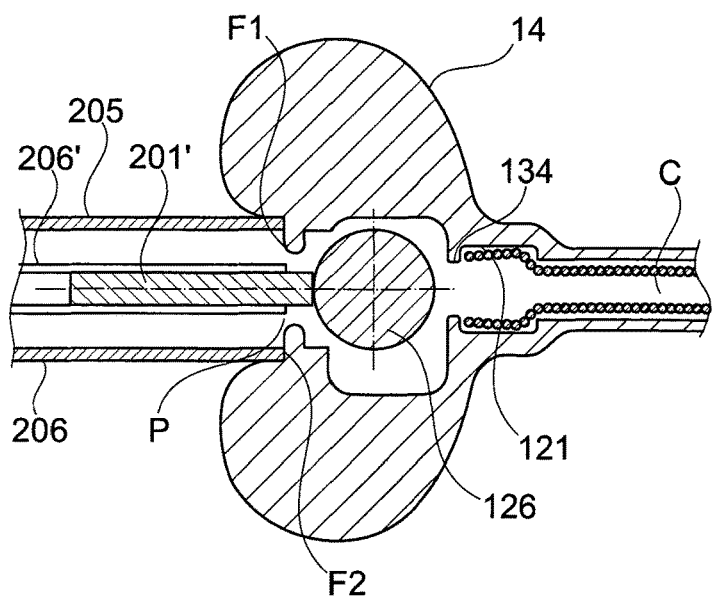

FIG. 8a shows yet another embodiment wherein the wall 206 of the housing 205 is of a flexible material and of an elongated tubular configuration, allowing the housing 205 to be bent as required to permit a directional control of the urine discharge. In this embodiment the housing 205 has open opposite first and second ends, with the aforementioned body 201' of a magnetically attractive material located centrally at the first end 202 in a central support structure 206' connected to peripheral wall 206; urine flowing along the length of the housing 205 inside thereof is discharged at the second end shown to the left in FIG. 8a. As seen best in FIG. 8b, the peripheral wall 206 of the housing 205 may be shaped at the first end 202 with an end face F2 configured to mate with another face F1 on the distal end portion 102 of the catheter device 100, thus establishing an interface which in the shown example extends perpendicular to the direction of flow of urine; direct inflow of urine into the housing 205 via passage P occurs as the magnetic valve body 126 is drawn towards the body 201', away from the valve seat 134 and the metal coil 121, which—by the properties, such as mass, of the body 201' applies the smallest attractive force onto the magnetic valve body 126. In FIG. 8b the distal end portion 102 of the catheter device 100 is configured to receive the first open end 202, thereby providing lateral support to the housing 205; faces F1, F2 need not contact.

The invention claimed is:

1. A urine flow control system, comprising:
   a catheter device configured for insertion into a urethra, the catheter device including (1) a proximal end portion and an opposite distal end portion, (2) a conduit between the proximal end portion and the distal end portion, the conduit having a urine inlet opening at the proximal end portion and a urine outlet opening at the distal end portion, (3) a valve seat at the distal end portion, and (4) a magnet configured as a valve body that is magnetically biased toward a closed position against the valve seat to block an outflow of urine from the catheter device through the urine outlet opening; and
   a magnetic actuator device configured for magnetically displacing the valve body from the valve seat to permit the outflow of urine from the catheter device through the urine outlet opening, wherein the magnetic actuator device comprises:
     a housing with (1) a first open end removably coupled to the distal end portion of the catheter device so as to receive the outflow of urine from the catheter device, and (2) a second open end configured for discharging the urine from the housing; and
     an actuator element at the first open end of the housing and comprising a body of a magnetically attractive material, wherein the actuator element is operable to move the valve body toward an open position when the distal end portion of the catheter device is coupled to the first open end of the housing.

2. The system of claim 1, wherein the first open end of the housing is configured for receiving the distal end portion of the catheter device.

3. The system of claim 1, wherein the distal end portion of the catheter device is configured for receiving the first open end of the housing.

4. The system of claim 1, wherein the distal end portion of the catheter device and the first open end of the housing have mating faces.

5. The system of claim 1, wherein the urine outlet opening of the conduit is located to a side of the catheter device and is configured to provide a sideways flow of urine.

6. The system of claim 1, wherein the urine outlet opening of the conduit is located at the distal end portion end of the catheter device and is configured to provide an axial flow of urine.

7. The system of claim 1, wherein the actuator element is located inside the housing.

8. The system of claim 1, wherein the housing includes a housing subportion defining a compartment that contains the actuator element.

9. The system of claim 1, wherein the housing includes a passage extending between the first open end of the housing and the second open end of the housing, the passage including a portion defined between the actuator element and a wall portion of the housing.

10. The system of claim 1, wherein the housing includes a chamber configured for storing the discharged urine.

11. The system of claim 1, wherein the housing is flexible and of an elongated tubular configuration, allowing the housing to be bent to permit a directional control of urine discharged from the catheter device and from the second open end of the housing.

\* \* \* \* \*